(12) United States Patent
Seo et al.

(10) Patent No.: US 10,184,903 B2
(45) Date of Patent: Jan. 22, 2019

(54) DEVICE FOR EVALUATING CRYSTALLINITY AND METHOD OF EVALUATING CRYSTALLINITY

(71) Applicant: Samsung Display Co. Ltd., Yongin (KR)

(72) Inventors: Jin Seo, Osan-si (KR); Yong Jun Park, Yongin-si (KR); Jong Soo Lee, Asan-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 6 days.

(21) Appl. No.: 15/097,514

(22) Filed: Apr. 13, 2016

(65) Prior Publication Data

US 2017/0074806 A1   Mar. 16, 2017

(30) Foreign Application Priority Data

Sep. 11, 2015  (KR) .................. 10-2015-0128703

(51) Int. Cl.
  *G01N 21/95*  (2006.01)
  *G01N 21/21*  (2006.01)

(52) U.S. Cl.
  CPC .......... *G01N 21/9505* (2013.01); *G01N 21/21* (2013.01); *G01N 2021/216* (2013.01); *G01N 2201/0683* (2013.01)

(58) Field of Classification Search
  CPC .............. G01N 21/21; G01N 21/9501; G01N 21/9505; G01N 2201/0683; G01N 2021/4792; G01N 21/23; G01N 2021/8848; G01N 2021/216; G01N 2021/217; G01N 2021/8825; G01J 4/04; G01J 4/00; G01J 3/0224
  See application file for complete search history.

(56) References Cited

U.S. PATENT DOCUMENTS

| | | | |
|---|---|---|---|
| 4,450,542 A | 5/1984 | Kritz | |
| 6,128,084 A * | 10/2000 | Nanbu | G01N 21/21 250/225 |
| 6,373,614 B1 * | 4/2002 | Miller | G01J 1/26 250/201.1 |
| 6,515,745 B2 * | 2/2003 | Vurens | G01J 4/04 250/225 |
| 6,753,961 B1 * | 6/2004 | Norton | G01J 3/447 356/364 |

(Continued)

FOREIGN PATENT DOCUMENTS

KR   101273739   9/2011

OTHER PUBLICATIONS https://www.microscopyu.com/techniques/polarized-light/polarized-light-microscopy (2003).*

(Continued)

*Primary Examiner* — Mohamed K Amara
(74) *Attorney, Agent, or Firm* — Cantor Colburn LLP

(57) ABSTRACT

A device for evaluating crystallinity includes a substrate holder configured to fix a polycrystalline silicon substrate thereon, a light source disposed below the substrate holder, a circular polarizing plate disposed above the polycrystalline silicon substrate, and a camera disposed above the circular polarizing plate and configured to capture an image transmitted through the circular polarizing plate.

14 Claims, 19 Drawing Sheets

(56) References Cited

U.S. PATENT DOCUMENTS

| | | | |
|---|---|---|---|
| 6,798,511 B1* | 9/2004 | Zhan | G01J 4/00 356/369 |
| 7,289,211 B1* | 10/2007 | Walsh, Jr. | A61B 5/0086 356/369 |
| 7,411,677 B2* | 8/2008 | Kawakami | G01J 4/04 356/364 |
| 7,505,134 B1* | 3/2009 | Johs | G01N 21/21 356/369 |
| 7,522,288 B2* | 4/2009 | De Groot | G01B 11/2441 356/497 |
| 7,527,200 B2 | 5/2009 | Tsikos et al. | |
| 7,839,506 B2* | 11/2010 | Straaijer | G01B 11/0641 356/369 |
| 7,859,661 B2* | 12/2010 | Ossikovski | G01J 3/02 356/301 |
| 7,889,339 B1* | 2/2011 | Flock | G01N 21/211 356/364 |
| 7,897,406 B2* | 3/2011 | Pinet | G01N 21/23 422/401 |
| 8,004,675 B2* | 8/2011 | Lefaudeux | G01J 4/04 356/364 |
| 8,279,439 B2* | 10/2012 | Gomi | G01N 21/23 356/364 |
| 8,334,977 B2* | 12/2012 | Fukazawa | G01N 21/21 356/369 |
| 8,792,096 B2* | 7/2014 | Straaijer | G01B 11/0641 356/369 |
| 8,830,481 B2* | 9/2014 | Hall | G01N 21/21 356/491 |
| 8,873,054 B2* | 10/2014 | Kandel | G01N 21/956 356/369 |
| 9,347,832 B2* | 5/2016 | Bodkin | G01J 4/04 |
| 2003/0019931 A1* | 1/2003 | Tsikos | G02B 26/10 235/454 |
| 2004/0156051 A1* | 8/2004 | Takeuchi | G01J 4/00 356/364 |
| 2004/0207845 A1* | 10/2004 | Opsal | G01B 11/0641 356/369 |
| 2004/0235205 A1* | 11/2004 | Levy | G01N 21/211 438/14 |
| 2010/0004875 A1* | 1/2010 | Urano | G01N 21/4738 702/40 |
| 2010/0103417 A1* | 4/2010 | Otani | G01N 21/21 356/364 |
| 2010/0231911 A1* | 9/2010 | Fischer | G01J 4/02 356/364 |
| 2011/0109906 A1* | 5/2011 | Liphardt | G01N 21/01 356/400 |
| 2011/0227558 A1* | 9/2011 | Mannion | B82Y 30/00 324/71.1 |
| 2013/0021609 A1* | 1/2013 | Lo | G01J 4/04 356/369 |
| 2016/0154156 A1* | 6/2016 | Ichihashi | G02B 5/3016 356/364 |
| 2017/0276597 A1* | 9/2017 | Emoto | G01N 21/23 |

OTHER PUBLICATIONS https://www.microscopyu.com/applications/live-cell-imaging/the-automatic-microscope (2006).*

* cited by examiner

[Fig 1]
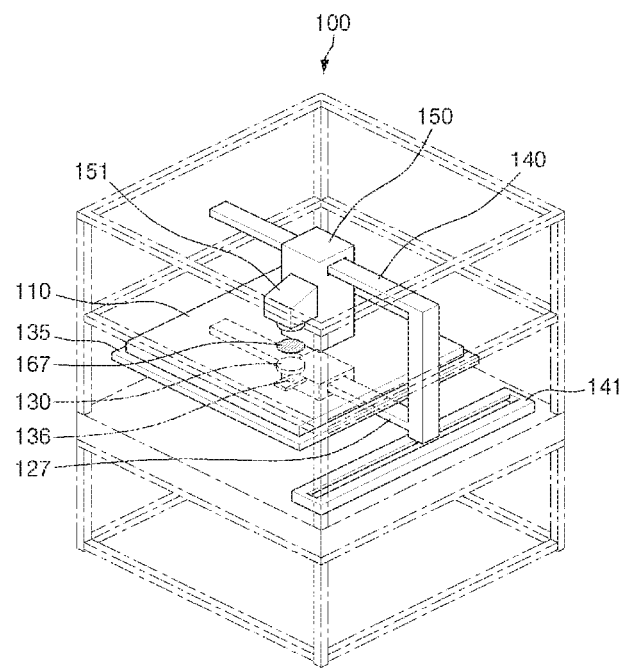

[Fig 2]
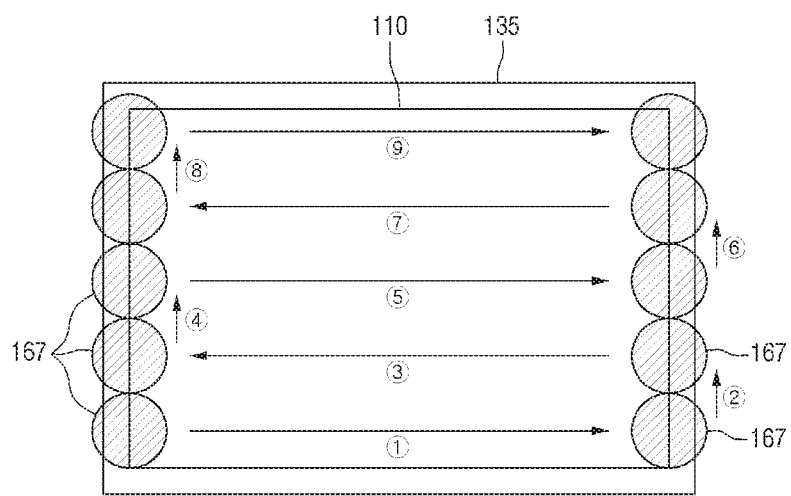

[Fig 3]
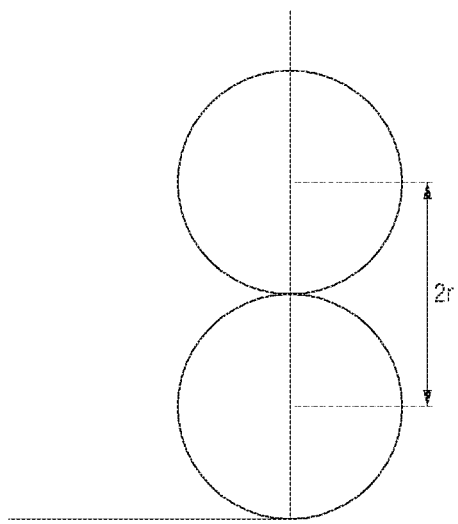

[Fig 4]
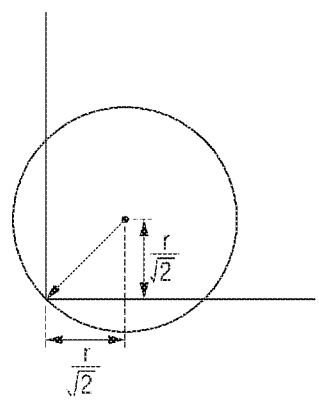

[Fig 5]
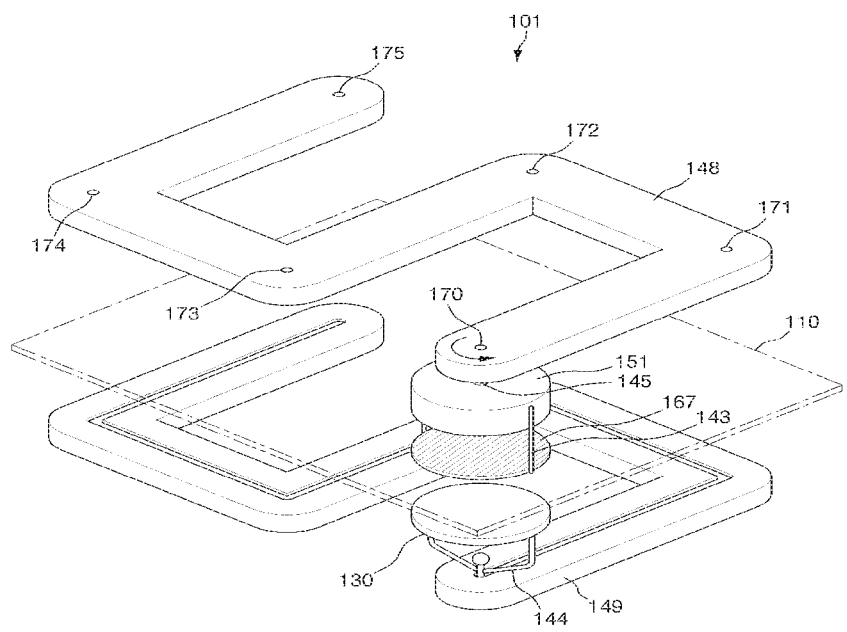

[Fig 6]
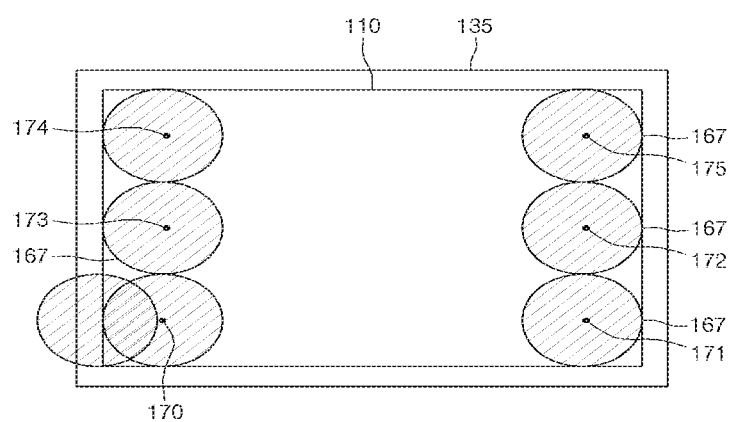

[Fig 7]
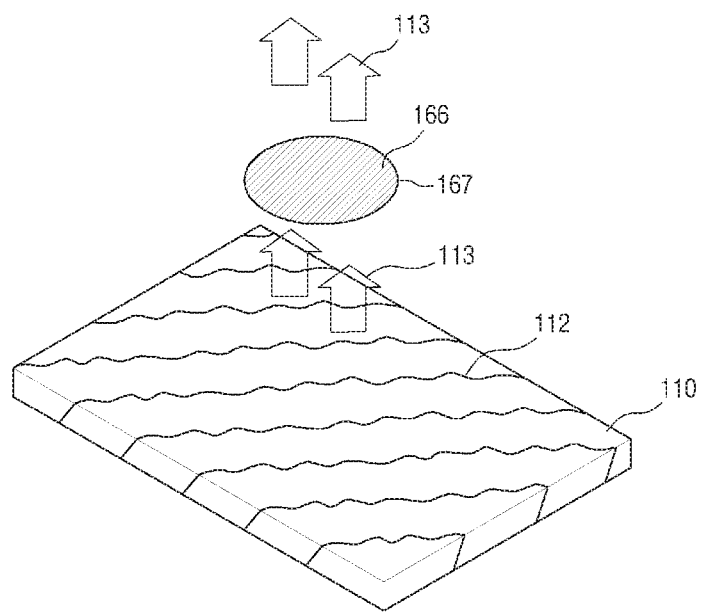

[Fig 8]
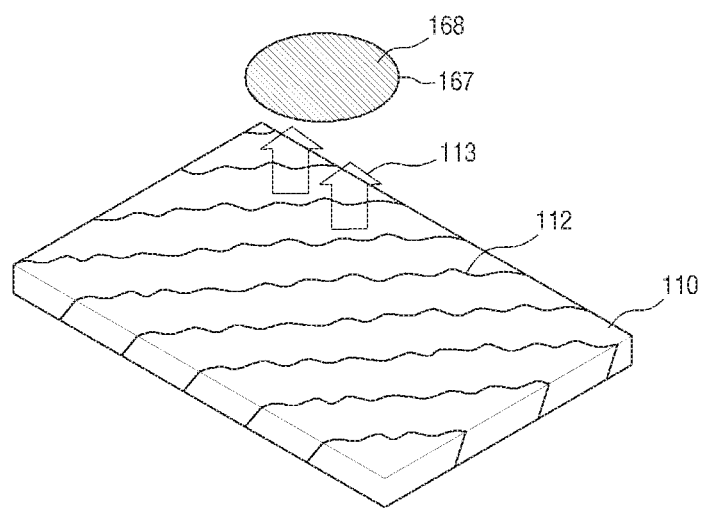

[Fig 9]
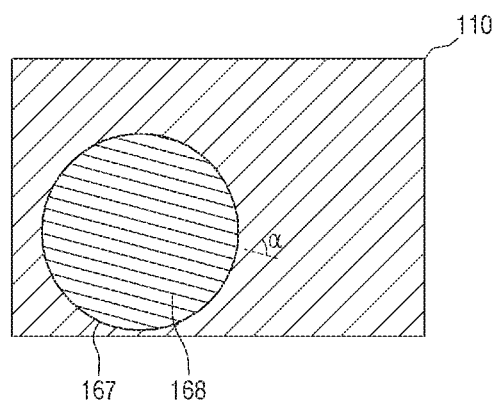

[Fig 10]
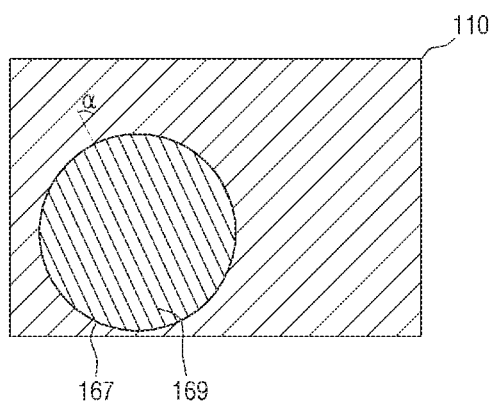

[Fig 11]
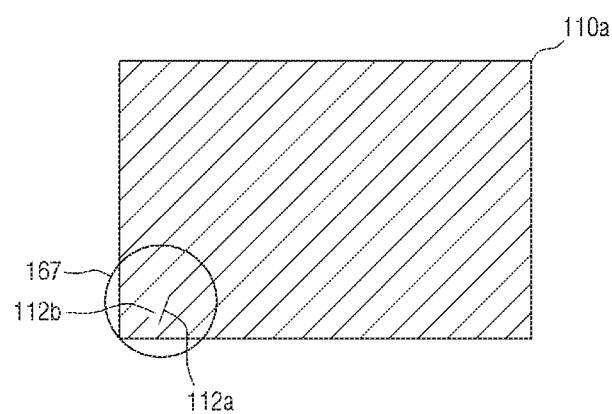

[Fig 12]
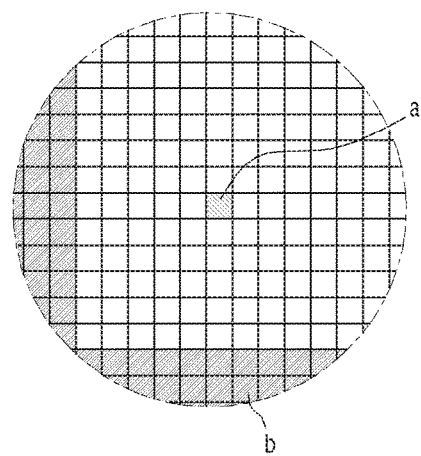

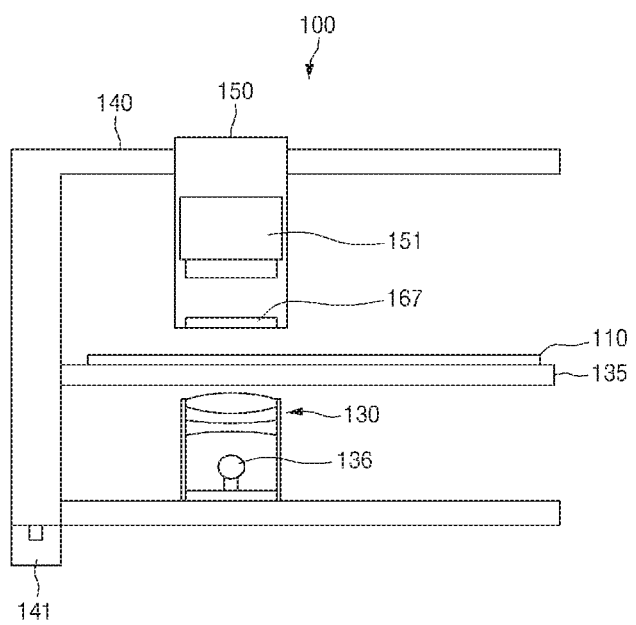
[Fig 13]

[Fig 14]
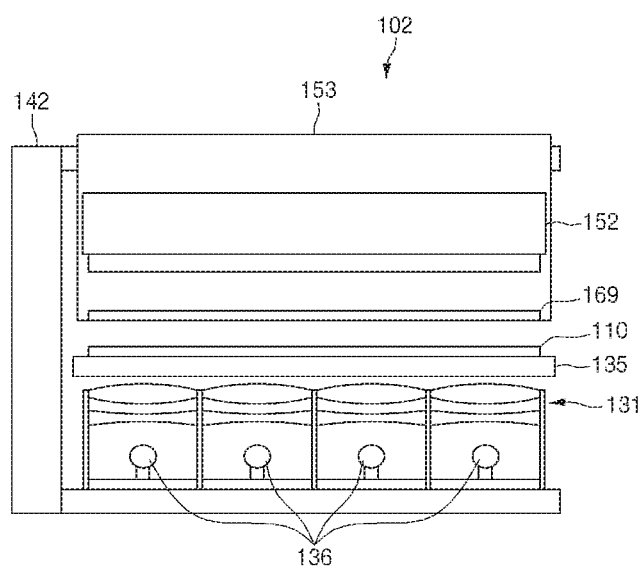

[Fig 15]
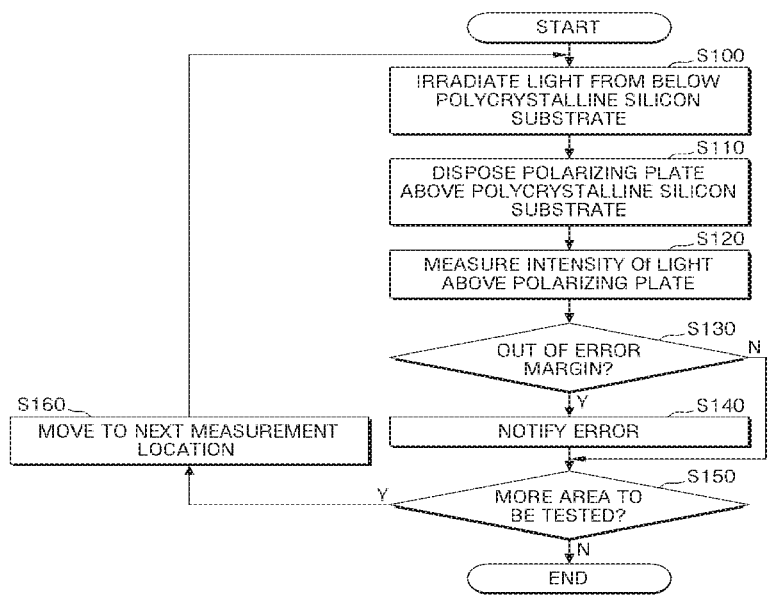

[Fig 16]
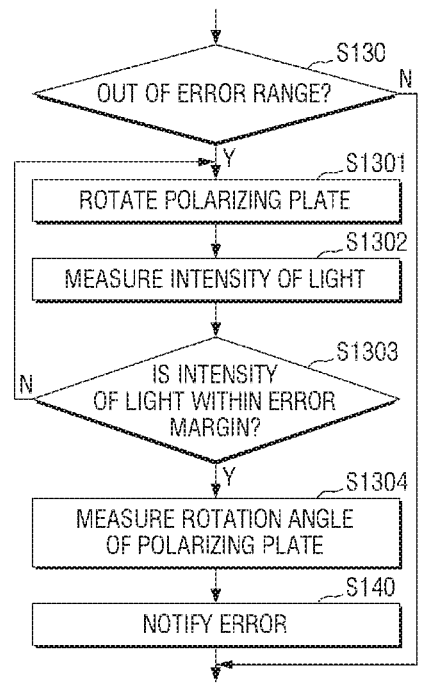

[Fig 17]
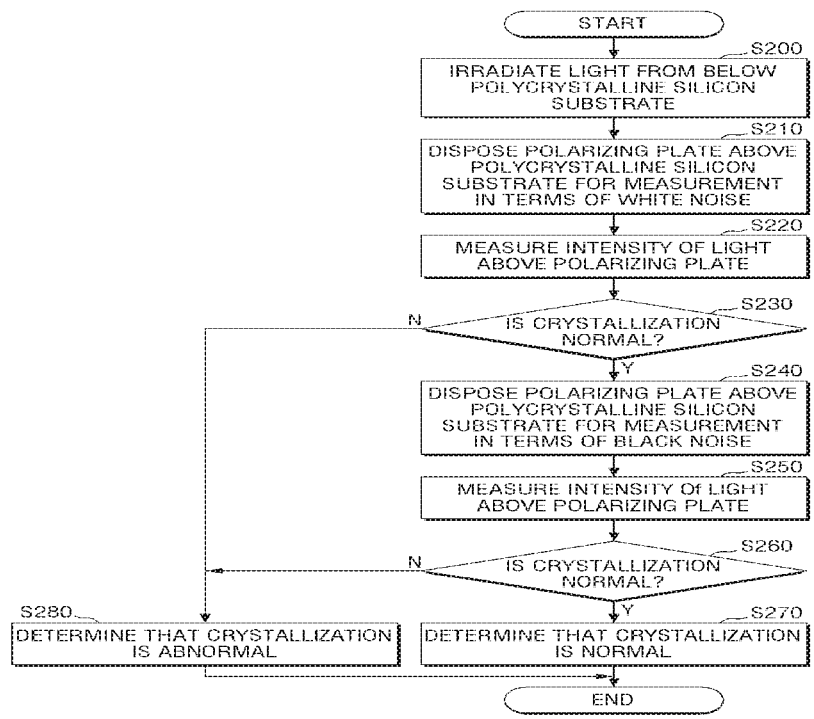

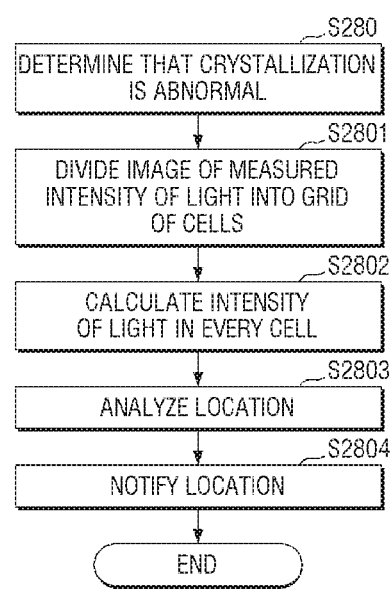
[Fig 18]

[Fig 19]
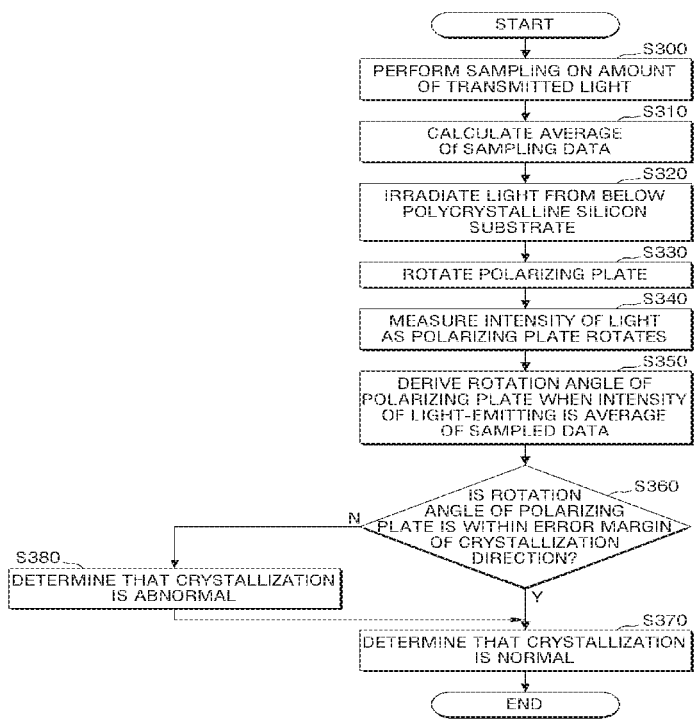

DEVICE FOR EVALUATING CRYSTALLINITY AND METHOD OF EVALUATING CRYSTALLINITY

This application claims priority to Korean Patent Application No. 10-2015-0128703, filed on Sep. 11, 2015, and all the benefits accruing therefrom under 35 U.S.C. § 119, the content of which in its entirety is incorporated herein by reference.

BACKGROUND

1. Field

The invention relates to a device for evaluating crystallinity, and a method of evaluating crystallinity.

2. Description of the Related Art

A thin-film transistor ("TFT") is a type of field effect transistors, which is produced by depositing thin films of semiconductor on an insulative supporting substrate. Similarly to other field effect transistors, a TFT has three terminals, i.e., a gate terminal, a drain terminal and a source terminal. One of main functionalities of a TFT is switching operation. A TFT is used in sensors, memories, optical devices, etc. In flat display devices, a TFT is used as a pixel switching element or a driving switching element.

As displays become larger and have increased quality, such elements are also required to have increased performance. Accordingly, a technology to produce a high-performance TFT having higher electron mobility than an amorphous silicon TFT having an electron mobility from 0.5 $cm^2/Vs$ to 1 $cm^2/Vs$. In this regard, a polycrystalline silicon TFT (poly-Si TFT) exhibits much higher performance than existing amorphous silicon TFTs. As a polycrystalline silicon TFT has an electron mobility ranging from several tens cm2/Vs to several hundreds cm2/Vs, it enables a data driving circuit or other peripherals requiring high electron mobility to be incorporated in a substrate. Further, the size of a polycrystalline silicon TFT is small, and thus the aperture ratio of a screen may be increased. In addition, since a driving circuit is incorporated in a substrate, there is no limit on line pitch for connecting the driving circuits as more pixels are disposed. As a result, high resolution may be achieved, driving voltage and power consumption may be saved, and deterioration of elements may be greatly suppressed.

As a technology to produce a polycrystalline silicon TFT, excimer laser crystallization ("ELC") technique that crystallizes amorphous silicon to form polycrystalline silicon is under development. In this regard, in order to control a polycrystalline silicon TFT produced through such a crystallization process, it is important to check when the crystallization direction is uniform and when there is a bump such as a protrusion or a bank.

Unfortunately, it is difficult to observe crystallinity of polycrystalline silicon with the naked eyes and there is a limit on an error margin, and thus it is necessary to determine the crystalline direction of polycrystalline silicon. Under the circumstances, what is required is a device for evaluating crystallinity.

SUMMARY

It is difficult to observe crystallinity of polycrystalline silicon with the naked eyes and there is a limit on an error margin, and thus it is necessary to determine the crystalline direction of polycrystalline silicon. Under the circumstances, what is required is a device for evaluating crystallinity.

In order to determine crystallization direction by measuring the amount of light having passed a gap between crystals of polycrystalline silicon, a polarizing plate is commonly used. Typically, a polarizing plate is smaller than a test target, i.e., a polycrystalline silicon substrate, and thus there may be a missing area from which crystallization direction of the polycrystalline silicon cannot be determined even by moving the polarizing plate.

Exemplary embodiments of the invention provide a device for evaluating crystallinity of polycrystalline silicon including a polarizing plate which may reduce time for evaluation, and a method of evaluating crystallinity.

Exemplary embodiments of the invention also provide a device for evaluating crystallinity capable of precisely determining an error in a crystal of polycrystalline silicon by carrying out both white noise and black noise tests, and a method of evaluating crystallinity.

Exemplary embodiments of the invention also provide a device for evaluating crystallinity capable of identifying a location of polycrystalline silicon where an error takes place to thereby determine a cause of the error during a manufacturing processing of the polycrystalline silicon, and a method of evaluating crystallinity.

According to an exemplary embodiment of the invention, a device for evaluating crystallinity is provided. A device for evaluating crystallinity, comprising a substrate holder configured to fix a polycrystalline silicon substrate thereon, a light source disposed below the substrate holder, a circular polarizing plate disposed above the polycrystalline silicon substrate, and a camera disposed above the polarizing plate and configured to capture an image transmitted through the polarizing plate, where the substrate holder includes a transparent material and transmits light emitted from the light source disposed below the substrate holder, where the light source is a laser light source, and where the device further comprises a beam expander for expanding light emitted from the laser light source, where the polarizing plate is rotatable on its center, and the camera is configured to measure a rotation angle of the polarizing plate when a captured image is brightest among images captured as the polarizing plate rotates, where the polarizing plate is rotatable on its center, and the camera is configured to measure a rotation angle of the polarizing plate when a captured image is darkest among images captured as the polarizing plate rotates, where it is determined that crystallization is abnormal when the rotation angle of the polarizing plate is out of an error margin for a predetermined crystallization direction.

In an exemplary embodiment, where the polarizing plate has slits defined in a predetermined crystallization direction, where the device further comprises a first guide line disposed at a first side of the substrate holder, a second guide line connected to and moving along the first guide line, and a movement guide moving along the second guide line and connecting the polarizing plate with the camera vertically, and where the movement guide moves along the second guide line and the second guide line moves along the first guide line, such that the polarizing plate and the camera are movable throughout an entire area of the polycrystalline silicon substrate, where the movement guide allows the polarizing plate to rotate at its current location, and where the device further comprises a control unit configured to determine a crystallization direction based on an intensity of light changing as the polarizing plate is rotated.

In an exemplary embodiment, where it is determined that the crystallinity is abnormal when an intensity measured by the camera is out of an error margin of a predetermined intensity of light.

In an exemplary embodiment, where an image captured by the camera covers an entire area of the polarizing plate.

In an exemplary embodiment, where the camera is configured to divide the captured image into a grid of cells to calculate an intensity of light in each of the cells, and it is determined that a crystallinity in a cell is abnormal when a calculated intensity of light of the cell is out of an error margin of a predetermined intensity of light.

In an exemplary embodiment, where the light source comprises a plurality of light sources disposed below the polycrystalline silicon substrate at a regular spacing, and the polarizing plate has such an area that it covers the polycrystalline silicon substrate.

According to an exemplary embodiment of the other invention, a method of evaluating crystallinity is provided. A method of evaluating crystallinity, the method comprising irradiating light from below a polycrystalline silicon substrate, allowing the irradiated light to pass through the polycrystalline silicon substrate and a polarizing plate disposed above the polycrystalline silicon substrate, measuring an intensity of light having passed through the polarizing plate at a location vertically above the polarizing plate, and notifying that there is an error in a crystallinity of the polycrystalline silicon substrate when the measured intensity of the light is out of an error margin of a predetermined criterion intensity of light.

In an exemplary embodiment, the method comprising when it is notified that there is an error in crystallinity of the polycrystalline silicon substrate, rotating the polarizing plate and measuring a rotation angle of the polarizing plate when a measured intensity of light is within the error margin of the predetermined criterion intensity of the light.

In an exemplary embodiment, the method comprising when the measured intensity of light is within the error margin of the predetermined criterion intensity of light, repeating moving the polarizing plate on the polycrystalline silicon substrate to measure crystallinity, where the predetermined criterion intensity of light comprises a white noise criterion and a black noise criterion, and where the method further comprises measuring an intensity of transmitted light from the polarizing plate at a location vertically above the polarizing plate in terms of the white noise criterion, measuring an intensity of transmitted light from the polarizing plate at a location vertically above the polarizing plate in terms of the black noise criterion when the measured intensity of light is within an error margin of a predetermined white noise criterion, and determining that crystallinity of the polycrystalline silicon substrate is normal when the measured intensity of light is within an error margin of a predetermined black noise criterion.

In an exemplary embodiment, where the notifying the error in crystallinity of the polycrystalline silicon substrate comprises dividing the measured intensity of light into a grid of cells, calculating an intensity of light in each of the cells, identifying a location of the polycrystalline silicon substrate where an error in crystallinity has taken place based on the intensity of light, and providing the location of the polycrystalline silicon substrate.

According to another exemplary embodiment of the invention, a method of evaluating crystallinity is provided. A method of evaluating crystallinity, the method comprising irradiating light from below a polycrystalline silicon substrate, receiving a criterion value for an amount of light having passed through the polycrystalline silicon substrate, rotating a polarizing plate above the polycrystalline silicon substrate to measure a rotation angle of the polarizing plate when the criterion value is obtained, and determining whether the rotation angle of the polarizing plate is within a normal range from a crystallization direction of the polycrystalline silicon substrate.

In an exemplary embodiment, where the determining comprises rotating the polarizing plate by ninety degrees to measure the amount of the light again when the measured rotation angle of the polarizing plate is within the normal range in the crystallization direction of the polycrystalline silicon substrate.

According to an exemplary embodiment of the invention, it is possible to reduce a time for evaluating crystallinity by using a different shape of polarizing plate.

In addition, according to an exemplary embodiment of the invention, both of white noise and black noise tests may be carried out in a single test device by rotating a polarizing plate.

Moreover, according to an exemplary embodiment of the invention, it is possible to determine a location of a substrate where crystallization is not normal and provide data that may be used a subsequent process of manufacturing polycrystalline silicon.

BRIEF DESCRIPTION OF THE DRAWINGS

The above and other exemplary embodiments and features of the invention will become more apparent by describing in detail exemplary embodiments thereof with reference to the attached drawings, in which:

FIG. 1 is a view schematically showing an exemplary embodiment of a device for evaluating degree of crystallinity according to the invention;

FIGS. 2 to 4 are views for conceptually illustrating an exemplary embodiment of processes of evaluating crystallinity of polycrystalline silicon by a device for evaluating crystallinity according to the invention;

FIG. 5 is a view schematically showing another exemplary embodiment of a device for evaluating degree of crystallinity according to the invention;

FIG. 6 is a view for illustrating exemplary embodiments obtaining sampling data prior to evaluating crystallinity of polycrystalline silicon substrate according to of the invention;

FIG. 7 is a view for illustrating a method of evaluating crystallinity of a polycrystalline silicon substrate in terms of white noise;

FIG. 8 is a view for illustrating a method of evaluating crystallinity of a polycrystalline silicon substrate in terms of black noise;

FIGS. 9 and 10 are schematic views for illustrating an exemplary embodiment of a method of determining crystallization direction of a polycrystalline silicon substrate according to the invention;

FIG. 10 is a view schematically showing another exemplary embodiment of a device for evaluating degree of crystallinity according to the invention;

FIGS. 11 and 12 views for illustrating a method for identifying a location where crystallization is abnormal when crystallinity of a polycrystalline silicon substrate is abnormal;

FIGS. 13 and 14 are cross-sectional views of exemplary embodiments of devices for evaluating crystallinity according to the invention;

FIG. 15 is a flow chart for illustrating an exemplary embodiment of a method of evaluating crystallinity of a polycrystalline silicon substrate according to the invention;

FIG. 16 is a flow chart for illustrating operations that may be additionally performed after it is determined that the crystallinity is out of an error margin in an operation S130 of FIG. 15;

FIG. 17 is a flow chart for illustrating another exemplary embodiment of a method of evaluating crystallinity of a polycrystalline silicon substrate according to the invention;

FIG. 18 is a flow chart for illustrating sub-operations of an operation S280 of FIG. 17; and FIG. 19 is a flow chart for illustrating another exemplary embodiment of a method of evaluating crystallinity of a polycrystalline silicon substrate according to the invention.

DETAILED DESCRIPTION

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this invention will be thorough and complete, and will fully convey the scope of the invention to those skilled in the art. Like reference numerals refer to like elements throughout.

It will be understood that when an element is referred to as being "on" another element, it can be directly on the other element or intervening elements may be therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. In an exemplary embodiment, when the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, when the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. In an exemplary embodiment, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the claims.

Referring to FIG. 1, a device 100 for evaluating crystallinity according to an exemplary embodiment of the invention may mainly include a substrate holder 135 and a first guide rail 141, for example.

FIG. 1 is a view schematically showing a device for evaluating crystallinity according to an exemplary embodiment of the invention.

Referring to FIG. 1, the device 100 for evaluating crystallinity according to the exemplary embodiment of the invention includes a substrate holder 135, a first guide rail 141, a second guide rail 140, a movement guide 150, a camera 151, a polarizing plate 167, a light source 136, and a beam expander 130.

The device 100 may be used for evaluating crystallinity of crystallized amorphous silicon to determine whether there is a fault. The device 100 may further include an element for bringing/taking a polycrystalline silicon substrate 110 inside or outside of a chamber in the device 100.

In an exemplary embodiment, the substrate holder 135 may have a large quadrangular shape secured to the chamber in the device 100, for example. While the first guide rail 141 and the second guide rail 140 move, the substrate holder 135 may be stationary during the evaluation of crystallinity. The substrate holder 135 is larger than the polycrystalline silicon substrate 110 so that the substrate holder 135 overlaps an entirety of the polycrystalline silicon substrate 110 in a plan view. In the device 100, light is irradiated from below the polycrystalline silicon substrate 110 and the amount of light having passed through the polycrystalline silicon substrate 110 are measured. Accordingly, the substrate holder 135 may include a transparent and rigid material to support the polycrystalline silicon substrate 110.

The first guide rail 141 may be disposed under the substrate holder 135 in a cross section, and may be spaced apart from a first side of the substrate holder 135 by a predetermined distance and parallel to the first side of the substrate holder 135 in a plan view. In an exemplary embodiment, the first guide rail 141 has a rail-like shape, for example, and a groove is defined in a center of the first guide rail 141 so that the second guide rail 140 moves along the first guide rail 141. The second guide rail 140 is engaged with the groove so that it may move along the first guide rail 141.

The second guide rail 140 may include arms extending above and under the substrate holder 135, and a support for supporting the arms and being connected to the first guide rail 141. The arms of the second guide rail 140 extending above and under the substrate holder 135 may be disposed at the same location on the vertical line passing through the substrate holder 135. Accordingly, the camera 151 and the polarizing plate 167 connected to the upper arm of the second guide rail 140 and the light source 136 and the beam expander 130 connected to the lower arm of the second guide rail 140 may be disposed on the same vertical line.

A groove is defined in the center of each of the upper arm and the lower arm of the second guide rail 140. The movement guide 150 is connected to the grooves such that it may move along the second guide rail 140. A lower end of the support of the second guide rail 140 protrudes and is connected to the groove of the first guide rail 141 such that the second guide rail 140 may move along the first guide rail 141.

An area of the movement guide 150 protrudes to be connected to the grooves in the arms of the second guide rail 140. The movement guide 150 includes the camera 151 and the polarizing plate 167 attached to an upper part of the movement guide 150, and further includes the light source 136 and the beam expander 130 attached to a lower part of the movement guide 150. The movement guide 150 aligns the camera 151, the polarizing plate 167, the light source 136 and the beam expander 130 on a vertical line in a vertical cross-section of the device 100. In order to move the camera 151, the polarizing plate 167, the light source 136 and the beam expander 130 in a direction parallel to a second side of the substrate holder 135 which is substantially perpendicular to the first side of the substrate holder 135 in a plan view to evaluate crystallinity, the movement guide 150 may move along the second guide rail 140. In addition, in order to move the camera 151, the polarizing plate 167, the light source 136 and the beam expander 130 in a direction perpendicular to the first side of the substrate holder 135 to evaluate crystallinity, the second rail 140 may move along the first guide rail 141.

Slits are defined in the polarizing plate 167 so that only some of light transmitted from the polycrystalline silicon substrate 110 that has a particular optical axis pass through the polarizing plate 167. As the polarizing plate 167 rotates above the polycrystalline silicon substrate 110, the amount of transmitted light changes depending on the rotation angle, so that the measured intensity of light changes. The measured intensity of light becomes the maximum when the direction in which the slits of the polarizing plate 167 are provided is parallel to the crystallization direction of the polycrystalline silicon substrate 110. On the contrary, the measured intensity of light becomes the minimum when the direction in which the slits of the polarizing plate 167 are provided is perpendicular to the crystallization direction of the polycrystalline silicon substrate 110. Therefore, it is possible to determine the crystallization direction of the polycrystalline silicon substrate 110 based on the direction in which the slits of the polarizing plate 167 are provided by measuring the intensity of transmitted light from the polarizing plate 167.

The crystallinity may be evaluated by aligning the slits of the polarizing plate 167 in the direction in which the polycrystalline silicon substrate 110 has to be crystallized. The above described process is referred to as evaluating crystallinity in terms of white noise. On the contrary, the crystallinity may be evaluated by aligning the slits of the polarizing plate 167 in the direction perpendicular to the direction in which the polycrystalline silicon substrate 110 has to be crystallized. The above described process is referred to as evaluating crystallinity in terms of black noise. In the device 100 shown in FIG. 1, once the slit direction of the polarizing plate 167 is aligned in the direction parallel to the crystallization direction or perpendicular to the crystallization direction, the polarizing plate 167 merely moves on the polycrystalline silicon substrate 110 but does not rotate. The white noise and the black noise will be described in more detail with reference to FIGS. 8 and 9.

In an exemplary embodiment, the polarizing plate 167 may have a circular shape, for example. Accordingly, the area in which the transmitted light from the polarizing plate 167 is captured by the camera 151 may also be circular, for example. The distance between a lens of the camera 151 and the polarizing plate 167 may be adjusted so that the polarizing plate 167 is included in an image captured by the camera 151.

The camera 151 measures the intensity of light above the polarizing plate 167. The camera 151 captures an image of the intensity of light. The control unit of the camera 151 divides the captured image into a grid of cells, and calculates the intensity of light in each of the cells. The control unit may compare the intensity of light in each of cells with a predetermined amount of transmitted light and may determine that crystallization is abnormal when the intensity of light in a cell is out of an error margin of the predetermined amount of transmitted light.

When it is determined that the crystallization of the polycrystalline silicon substrate 110 is abnormal, it is important to identify in which part of the crystallization process an error has taken place. In order to identify the cause of an error, it is important to find out the location where the polycrystalline silicon substrate 110 is abnormally crystallized. An abnormally crystallized polycrystalline silicon substrate 110 is frequently produced when the intensity or wavelength of laser is changed during the process of crystallizing an amorphous silicon substrate by irradiating laser onto it. Accordingly, in order to stop producing an abnormally crystallized polycrystalline silicon substrate 110, it is necessary to identify the location where the polycrystalline silicon substrate 110 has been abnormally crystallized and to estimate an error in laser at the location to adjust the intensity or wavelength of the laser.

In an exemplary embodiment, the light source 136 may be a laser light source emitting a short-wavelength laser, for example. The laser light source emits single-phase light and thus it has high resolution for identifying a location where the polycrystalline silicon substrate 110 is abnormally crystallized in the image captured by the camera 151. As single-phase light is output, the intensity of light reaching the camera increases. In addition, the laser light source reduces influence by interference or diffraction of light during the process of evaluating crystallinity compared to an LED light source, and thus accuracy in evaluating crystallinity may be increased.

Despite such advantages of employing a laser light source, the laser light source is a point light source, and thus it is necessary to increase the illumination area of the laser source. This is because it takes too long time to evaluate crystallinity using a point light source. For this reason, the beam expander 130 is employed for expanding the illumination area of the laser light source. The beam expander 130 includes a couple of a concave lens and a convex lens and expands the illumination area of a laser light source without changing the phase of light emitted from the laser light source.

Hereinafter, evaluating crystallinity by the device 100 shown in FIG. 1 will be described with reference to FIGS. 2 to 4. FIG. 2 is a view showing paths along which the polarizing plate 167 moves above the polycrystalline silicon substrate 110 for evaluating crystallinity.

Initially, the polarizing plate 167 is located at a corner of a first side of the polycrystalline silicon substrate 110. The camera 151 may be disposed vertically above the polarizing plate 167. The light source 136 may be disposed under the polycrystalline silicon substrate 110 vertically below the center of the polarizing plate 167. As the polarizing plate 167 moves along the paths shown in FIG. 2, the camera 151 and the light source 136 also move along the paths shown in FIG. 2.

In an exemplary embodiment, the center of the polarizing plate 167 is located above the first side of the polycrystalline silicon substrate 110. When the polarizing plate 167 is located such a start position, a part of the polarizing plate 167 is not involved in evaluating crystallinity. Despite such a part, the center of the polarizing plate 167 is located above the first side of the polycrystalline silicon substrate 110 in order to prevent any portion of the polycrystalline silicon substrate 110 from not being evaluated. When the center of the polarizing plate 167 is located more to the outside than the first side of the polycrystalline silicon substrate 110, it takes longer time to evaluate crystallinity than when it is located as shown in FIG. 2. On the contrary, when the center of the polarizing plate 167 is located more to the inside than the first side of the polycrystalline silicon substrate 110, there may be a portion of the polycrystalline silicon substrate 110 where crystallinity is not evaluated.

Referring to FIG. 2, evaluation may be initiated at a first corner where the first side of the polycrystalline silicon substrate 110 passes the center of the polarizing plate 167. Once the evaluation is completed, the polarizing plate 167 moves in the direction indicated by arrow ①. While the polarizing plate 167 moves in the direction indicated by arrow ①, the polarizing plate 167 is captured continuously, so that crystallinity is evaluated. After the camera 151 captures the intensities of the entire light having passed through the polarizing plate 167, and then divides an image into a grid of cells to identify a location where crystallization is abnormal only when the intensities of the light are below a predetermined amount of light. Then, the intensity of light may be calculated in each of the cells.

The polarizing plate 167 may move in the direction indicated by arrow ① until the center of the polarizing plate 167 passes the second side of the polycrystalline silicon substrate 110 opposed to the first side. After the polarizing plate 167 moves in the direction indicated by arrow ①, the polarizing plate 167 may move in the direction indicated by arrow ②. The direction indicated by arrow ① may be perpendicular to the direction indicated by arrow ②. The polarizing plate 167 moves in the direction indicated by arrow ② until the distance between the center of the polarizing plate 167 located at the end of the direction indicated by arrow ① and the center of the polarizing plate 167 having moved in the direction indicated by arrow ② becomes twice (2r) the radius of the polarizing plate 167.

After the polarizing plate 167 has moved in the direction indicated by arrow ②, it moves in the direction indicated by arrow ③ which is the opposite direction to the direction indicated by arrow ①. The polarizing plate 167 moves in the direction indicated by arrow ③ in the same manner as it moves in the direction indicated by arrow ①, evaluating crystallinity continuously.

The polarizing plate 167 may move in the directions indicated by arrows ①, ②, ③, ④, ⑤, ⑥, ⑦, ⑧ and ⑨ in the same manner, evaluating crystallinity of the polycrystalline silicon substrate 110 continuously. When the polarizing plate 167 moves in the directions indicated by arrows ②, ④, ⑥ and ⑧, crystallinity may be evaluated only before and after the movement, and not while the polarizing plate 167 is moving. However, when the polarizing plate 167 moves in the directions indicated by arrows ①, ③, ⑤, ⑦ and ⑨, crystallinity has to be evaluated continuously, in order to evaluate crystallinity throughout the entire area of the polycrystalline silicon substrate 110.

FIG. 4 is a view showing a location from which evaluation of crystallinity on the polarizing plate 167 is started according to another exemplary embodiment of the invention. In this device for evaluating crystallinity shown in FIG. 4, the polarizing plate 167 moves in the same directions shown in FIG. 2, evaluating crystallinity. However, the start location of evaluating crystallinity in this exemplary embodiment is different from that of the above exemplary embodiment, which will be described in detail.

The center of the polarizing plate 167 may located at a position distant from the corner of the polycrystalline silicon substrate 110 by a value defined by r divided by square root of two ($r/\sqrt{2}$) in the first side direction and the second side direction, respectively. The polarizing plate 167 may start evaluation from the position distant from the corner of the polycrystalline silicon substrate 110 by $r/\sqrt{2}$ in the first side direction and the second side direction, respectively, and may move in the directions indicated by arrows ①, ②, ③, ④, ⑤, ⑥, ⑦, ⑧ and ⑨ in the same manner as in FIG. 2, evaluating crystallinity of the polycrystalline silicon substrate 110. According to the exemplary embodiment shown in FIG. 4, however, the polarizing plate 167 has to evaluate crystallinity continuously even when it moves in the directions ②, ④, ⑥ and ⑧, in order to evaluate the entire area of the polycrystalline silicon substrate 110. According to the exemplary embodiment shown in FIG. 4, the distance by which the polarizing plate 167 moves in the directions indicated by arrows ①, ③, ⑤, ⑦ and ⑨ is shortened, and thus the evaluation time may be reduced.

FIG. 5 is an exploded perspective view for illustrating the relationship among a third guide rail 148, a fourth guide rail 149, a polarizing plate 167, a light source 136 of a device 101 for evaluating crystallinity according to another exemplary embodiment of the invention. The device 101 for evaluating crystallinity according to another exemplary embodiment of the invention may include the third guide rail 148, the fourth guide rail 149, a camera 151, a rotation shaft 145, the polarizing plate 167, a polarizing plate connector 143, a beam expander 130, the light source 136, and a beam expander fixture 144. In the device 101 for evaluating crystallinity according to the another exemplary embodiment, when the rotation shaft 145 reaches a first point 170, a second point 171, a third point 172, a fourth point 173, a fifth point 174 and a sixth point 175, it may rotate at the first point 170, the second point 171, the third point 172, the fourth point 173, the fifth point 174 and the sixth point 175. As the rotation shaft 145 rotates, the polarizing plate 167 and the camera 151 may rotate with it. As the polarizing plate 167 rotates, the direction of the slits changes, such that the intensity of light captured by the camera 151 also changes.

FIG. 6 is a view for illustrating obtaining sampling data prior to evaluating crystallinity of the polycrystalline silicon substrate 110. Referring to FIG. 6, prior to evaluating crystallinity of the polycrystalline silicon substrate 110, sampling data may be obtained at at least one of the first point 170, the second point 171, the third point 172, the fourth point 173, the fifth point 174 and the sixth point 175. The sampling data may be the slit direction of the polarizing plate 167 when the camera 151 captures the intensity of particular light, or may be the intensity of light captured by the camera 151 when the slit direction of the polarizing plate 167 is fixed in a particular direction. When a plurality of sampling data items is obtained, the average thereof may be calculated. The average may be set to be as a criterion value for evaluating crystallinity.

Referring back to FIG. 5, after determining the criterion value for evaluating crystallinity, the crystallinity of the polycrystalline silicon substrate 110 may be evaluated. The evaluation is performed along the third guide rail 148 and the fourth guide rail 149. The evaluation may be performed in the same manner as the exemplary embodiment shown in FIG. 1. That is, the slit direction of the polarizing plate 167 is fixed, and the criterion value is compared with the intensity of the light captured by the camera 151 to thereby determine whether the crystallization is normal or not.

FIG. 7 is a view for illustrating evaluating crystallinity in terms of white noise. Laser is irradiated onto an amorphous silicon substrate, so that a polycrystalline silicon substrate 110 having the crystallization direction as shown in FIG. 7 is produced. The crystallized silicon pieces are connected with one another like a chain. The polycrystalline silicon substrate 110 has a crystallization direction 112 as shown in FIG. 7. The crystallization direction 112 refers to a gap between crystallized silicon pieces observed as a boundary therebetween. When light is irradiated from below the polycrystalline silicon substrate 110, some of the light 113 may transmit via a gap between crystallized silicon pieces, i.e., a gap in the crystallization direction 112. The intensity of the transmitted light 113 in the crystallization direction 112 is larger than the remaining of the light. Since slits 166 are defined in the polarizing plate 167 in the crystallization direction, only the transmitted light 113 in the crystallization direction 112 may be measured. When the crystallization direction 112 is different from a predetermined crystallization direction, the amount of transmitted light 113 may be smaller than the amount of light measured from a silicon substrate having the normal crystallization direction. This is referred to as white noise.

Even when it is determined that the polycrystalline silicon substrate 110 is normal with reference to white noise in FIG. 7, it may be determined that the polycrystalline silicon substrate 110 is abnormal in terms of black noise in FIG. 8. Accordingly, it is necessary to perform evaluation of crystallization in terms of black noise on the polycrystalline silicon substrate 110 which was determined to be normal in terms of white noise.

Referring to FIG. 8, a method of evaluating crystallinity in terms of black noise will be described. When the slit direction of the polarizing plate 167 is oriented in a direction perpendicular to the crystallization direction 112, no intensity of transmitted light 113 via the polarizing plate 167 is supposed to be measured. In other words, no black noise is supposed to exist. When the measured intensity of light is higher than a criterion value even when the first slit direction 168 of the polarizing plate 167 is perpendicular to the crystallization direction 112, it is determined that there is block noise.

The criterion values for the white noise and the black noise may be determined from sampling data as in FIG. 6 or may be predetermined criterion values.

FIGS. 9 and 10 are views for illustrating a method of determining whether crystallization is normal based on an angle made by each of the first slit direction 168 and the second slit direction 169 of the polarizing plate 167 and the crystallization direction when an intensity of light is measured, according to another exemplary embodiment of the invention. Referring to FIGS. 9 and 10, the first slit direction 168 of the polarizing plate 167 is rotated above the polycrystalline silicon substrate 110, and the first slit direction 168 of the polarizing plate 167 may be measured when the camera captures light having a predetermined intensity. Here, it is assumed that the first slit direction 168 of the polarizing plate 167 when the particular intensity of light is measured is a. Although the first slit direction 168 of the polarizing plate 167 in FIG. 9 is different from that of FIG. 10, the measured intensity of light in FIG. 9 may be equal to that of FIG. 10. The crystallization direction 112 of the polycrystalline silicon substrate 110 may be determined based on the measured value a of FIGS. 9 and 10.

Accordingly, it may be determined that crystallinity is normal when the measured value a is within a predetermined error margin, and it may be determined that crystallinity is abnormal otherwise.

A method of determining a location of the polycrystalline silicon substrate 110a where crystallization is abnormal when the crystallinity is abnormal will be described with reference to FIGS. 11 and 12. The camera 151 is located above the polarizing plate 167 and measures the intensity of light 113 having passed through the polarizing plate 167. When there is provided an abnormal crystallization direction 112a or an area not normally crystallized 112b, a method of determining the location of the abnormal crystallization direction 112a or the location of the area not normally crystallized 112b will be described.

When there is an abnormal crystallization direction 112a, the measured intensity of the light in terms of black noise is above a predetermined intensity of light. When there is an area 112b not normally crystallized 112b, the measured intensity of the light in terms of white noise is below the predetermined intensity of light.

If there is a non-measured area b as shown in FIG. 12, crystallinity may be evaluated by calculating a ratio of the non-measured area b with respect to the total area and adjusting the criterion intensity of light according to the ratio. Those skilled in the art will appreciate how to adjust the criterion intensity of light according to the ratio.

Referring to FIG. 12, the measured intensity of the light may be divided into a gird of cells when the measured intensity of light is determined to be abnormal based on a criterion value. Intensity of light is measured in every cell of the grid, and the measured intensity of light in every cell is compared with the criterion value. When the value measured in cell a is out of an error margin of the criterion value, it is determined that cell a is an abnormal location. When the error is notified, the location may be notified together. When the decision is made when the intensity of light is measured in terms of white noise, the error indicates that an area 112b where crystallization is not normal has been found. When the decision is made when the intensity of light is measured in terms of black noise, the error indicates that an abnormal crystallization direction 112a has been found.

FIG. 13 is a cross-sectional view of the device 100 for evaluating crystallinity.

Referring to FIG. 13, the light source 136 may be integrated with the beam expander 130. The first guide rail 141 may move back and forth. The light source 136 and the beam expander 130 may move left and right along the second guide rail 140 connected to the first guide rail 141. The polycrystalline silicon substrate 110 is secured by the substrate holder 135.

The locations of the camera 151 and the polarizing plate 167 are adjusted so that they are disposed above the light source 136. The camera 151 and the polarizing plate 167 are attached to the movement guide 150 to move left and right along the second guide rail 140. In doing so, the control unit adjusts the locations of the movement guide 150 and the light source 136 so that the vertical center axis of the light source 136 is in line with the vertical center axis of the camera 150 and the polarizing plate 167.

The camera 151 may capture an image of light transmitted from the polycrystalline silicon substrate 110 at the current location and then may move aside. The movement guide 150 including the camera 151 may move to the right until the left side of the current location reaches the right side. The camera 151 may capture the polycrystalline silicon substrate 110 after it has moved to the next location. Such moving and capturing may be repeated until the camera 151 captures the images of the entire area of the polycrystalline silicon substrate 110.

FIG. 14 is a cross-sectional view of the device 102 for evaluating crystallinity.

Referring to FIG. 14, the camera 152 and the polarizing plate 169 may have such a size that they may cover the entire area of the polycrystalline silicon substrate 110. According to the exemplary embodiment shown in FIG. 14, the device 102 for evaluating crystallinity may include a plurality of light sources 136 and beam expanders 131 each for expanding laser light emitted from the respective light sources 136.

The plurality of light sources 136 may be spaced apart from one another at a regular spacing. Each of the beam expanders 131 includes a concave lens at its lower portion and a convex lens at its upper portion aligned with the vertical center axis of the respective lights 136. According to the example shown in FIG. 10, a location where crystallization is abnormal may be determined by capturing with the camera 151 at once, thereby saving processing time. When there is a plurality of abnormally crystallized areas, the polarizing plate 169 has to be rotated to determine the crystallization directions of the abnormally crystallized areas. In doing so, the camera 152 of the device 102 may capture the entire area of the polycrystalline silicon substrate 110, and thus the crystallization directions of the abnormally crystallized areas may be more clearly determined than in the example shown in FIG. 13. In the example shown in FIG. 13 where the polycrystalline silicon substrate 110 is divided into cells, a measured value may be less reliable when a location where crystallization is abnormal is found at a boundary between the cells. The intensity of light becomes weak away from the light source. When the intensity of light is weak, it is difficult to determine whether there is abnormal crystallization from an image captured by the camera 152.

In contrast, in the example shown in FIG. 14 where a number of light sources are connected to one another, light at a boundary between light sources is reinforced by light from the right and left light sources. As a result, the intensity of light may be stronger.

FIG. 15 is a flow chart for illustrating a method of evaluating crystallinity according to an exemplary embodiment of the invention. Referring to FIG. 15, light is irradiated from below a polycrystalline silicon substrate 110 (operation S100). In the device 100, a light source 136 may be disposed below the polycrystalline silicon substrate 110 to irradiate light. In order to measure only light 113 transmitted in the crystallization direction 112 of the polycrystalline silicon substrate 110, a slit direction 116 of a polarizing plate 167 is oriented in a direction parallel the crystallization direction 112 of the polycrystalline silicon substrate 110. The polarizing plate 167 is disposed on the polycrystalline silicon substrate 110 (operation S110). The camera 151 above the polarizing plate 167 measures the intensity of the transmitted light 113 (operation S120). When the intensity of the transmitted light 113 measured by the camera 151 above the polarizing plate 167 in operation S120 is out of an error margin (Yes in operation S130), an error is notified (operation S140). Then, it is determined whether there is any area of the polycrystalline silicon substrate 110 to be evaluated (operation S150). When so, the location of the camera is moved for capturing the area (operation S160). The camera may move, for example, along the paths according to the exemplary embodiment shown in FIG. 2.

If the intensity of the transmitted light 113 measured by the camera 151 above the polarizing plate 167 in operation S120 is within the error margin (No in operation S130), it is determined whether there is any area of the polycrystalline silicon substrate 110 to be evaluated (operation S150). When so, the location of the camera is moved for capturing the area (operation S160). The camera may move, for example, along the paths according to the exemplary embodiment shown in FIG. 2.

FIG. 16 is a flow chart for illustrating a process of evaluating crystallinity additionally performed prior to notifying an error in operation S140 when it is determined that the intensity of the transmitted light 113 is out of an error margin (Yes in operation S130).

If the intensity of the transmitted light 113 measured by the camera 151 above the polarizing plate 167 (operation S120) is out of an error margin (Yes in operation S130), the polarizing plate 167 may be rotated (operation S1301) and the intensity of light may be measured (operation S1302). When the measured intensity of light is with the error margin of the criterion value (Yes in operation S1303), the rotation angle of the polarizing plate 167 is measured (operation S1304). Since the rotation angle of the polarizing plate 167 may be the crystallization direction 112 of the polycrystalline silicon substrate 110, the rotation angle of the polarizing plate 167 may be notified together when the error is notified in operation S140.

FIG. 17 is a flow chart for illustrating a method of evaluating crystallinity according to another exemplary embodiment of the invention. Light emitted from a light source 136 is irradiated from below a polycrystalline silicon substrate 110 (operation S200). A polarizing plate 167 is disposed such that a slit direction 166 of the polarizing plate 167 is in parallel to a crystallization direction 112, so that the emitted light passes through the polycrystalline silicon substrate 110 for measurement in terms of white noise (operation S210). The intensity of transmitted light 113 is measured by the camera 151 above the polarizing plate 167 (operation S220). It is determined that the crystallinity is normal (Yes operation S230) when the intensity of the transmitted light 113 is within an error margin of a criterion intensity of light in terms of white noise. When it is determined that the crystallinity is normal in terms of white nose (Yes in operation S230), the crystallinity is measured in terms of black noise. The polarizing plate 167 is disposed such that the slit direction 166 of the polarizing plate 167 is perpendicular to a crystallization direction 112, so that the emitted light passes through the polycrystalline silicon substrate 110 for measurement in terms of black noise (operation S240). The camera 151 above the polarizing plate 167 measures the intensity of the transmitted light 113 in terms of black noise (operation S250). When the measured intensity of the transmitted light 113 is out of an error margin of a criterion intensity (No in operation S260), it is determined that crystallinity is abnormal (operation S280). When the measured intensity of the transmitted light 113 is with the error margin of the criterion intensity (Yes in operation S260), it is determined that crystallinity is normal (operation S270).

According to the method illustrated in FIG. 17, the crystallinity of the polycrystalline silicon substrate 110 is determined to be normal only when both the crystallinity evaluated in terms of white noise and the crystallinity evaluated in terms of black noise are normal.

FIG. 18 is a flow chart for illustrating operations that may be additionally performed after it is determined that the crystallinity is abnormal in an operation S280.

Referring to FIG. 18, the camera 151 measures the intensity of the entire transmitted light 113 from the polarizing plate 167. It is to be noted that, in comparing the intensity of the transmitted light 113 with a criterion value, the intensity of the entire transmitted light is compared, instead of the intensity of light in each of cells as shown in FIG. 12. When the polarizing plate 167 is located at a corner of the polycrystalline silicon substrate 110 as shown in FIG. 12, the intensity of light may be compared with an adjusted criterion intensity of light by the ratio of the non-measured area b to the entire area. When it is determined that the intensity of the transmitted light 113 from the overall polarizing plate 167 is abnormal, the image of the measured intensity of light is divided into a grid of cells as shown in FIG. 12 (operation S2801). The intensity of light is calculated in each of the cells (operation S2802). The intensity of light in each of the cells is compared with a criterion value, and a location where crystallization is abnormal is analyzed (operation S2803). The location where crystallization is abnormal is notified (operation S2804).

A method of evaluating crystallinity of the polycrystalline silicon substrate 110 according to another exemplary embodiment of the invention will be described with reference to FIG. 19.

The amount of transmitted light is sampled from at least one areas of the polycrystalline silicon substrate 110 of the device 101 shown in FIG. 5 when the slit direction 166 of the polarizing plate 167 is oriented at a particular direction (operation S300). When there is a plurality of samples of the amount of transmitted light, an average of the sampling data is calculated (operation S310). Light is irradiated from below the polycrystalline silicon substrate (operation S320).

The polarizing plate 167 is disposed above the polycrystalline silicon substrate on the vertical center axis of the light source, that the slit direction 166 of the polarizing plate 167 is rotated (operation S330). The camera measures the intensity of the transmitted light 113 while the polarizing plate 167 is rotating (operation S340). A rotation angle of the polarizing plate 167 is measured when a criterion value is obtained, which is the average of predetermined sampling data (operation S350). It is determined whether the measured rotation angle of the polarizing plate 167 is within an error margin of a predetermined rotation angle (operation S360). When the rotation angle is within the error margin (Yes in operation S360), it is determined that the crystallization is normal (operation S370). When the rotation angle is out of the error margin (No in operation S360), it is determined that the crystallization is abnormal (operation S380).

What is claimed is:

1. A device for evaluating crystallinity, comprising: a substrate holder which fixes a polycrystalline silicon substrate thereon; a light source disposed below the substrate holder; a polarizing plate having a circular shape and disposed above the polycrystalline silicon substrate; a camera which is disposed above the polarizing plate and captures an image transmitted through the polarizing plate, wherein, in a state where the polycrystalline silicon substrate is fixed, the light source, the polarizing plate and the camera configured to move along a first path extending in a first direction, and wherein, after the light source, the polarizing plate and the camera move along the first path, the light source, the polarizing plate and the camera are configured to move along a second path extending in a second direction crossing the first direction.

2. The device of claim 1, wherein the substrate holder includes a transparent material and transmits light emitted from the light source disposed below the substrate holder.

3. The device of claim 1, wherein the light source is a laser light source, and wherein the device further comprises a beam expander for expanding light emitted from the laser light source.

4. The device of claim 1, wherein the polarizing plate is rotatable on its center, and the camera measures a rotation angle of the polarizing plate when a captured image is brightest among images captured as the polarizing plate rotates.

5. The device of claim 4, wherein it is determined that crystallization is abnormal when the rotation angle of the polarizing plate is out of an error margin for a predetermined crystallization direction.

6. The device of claim 1, wherein the polarizing plate is rotatable on its center, and the camera measures a rotation angle of the polarizing plate when a captured image is darkest among images captured as the polarizing plate rotates.

7. The device of claim 6, wherein it is determined that crystallization is abnormal when the rotation angle of the polarizing plate is out of an error margin for a predetermined crystallization direction.

8. The device of claim 1, wherein the polarizing plate has slits defined in a predetermined crystallization direction, wherein the device further comprises: a first guide line disposed at a first side of the substrate holder; a second guide line connected to and moving along the first guide line; and a movement guide moving along the second guide line and connecting the polarizing plate with the camera vertically, and wherein the movement guide moves along the second guide line and the second guide line moves along the first guide line, such that the polarizing plate and the camera are movable throughout an entire area of the polycrystalline silicon substrate.

9. The device of claim 8, wherein the movement guide allows the polarizing plate to rotate at its current location, and wherein the device further comprises: a control unit which determines a crystallization direction based on an intensity of light changing as the polarizing plate is rotated.

10. The device of claim 1, wherein it is determined that the crystallinity is abnormal when an intensity measured by the camera is out of an error margin of a predetermined intensity of light.

11. The device of claim 1, wherein an image captured by the camera covers an entire area of the polarizing plate.

12. The device of claim 1, wherein the device determines an average of intensities of light measured by the camera above some areas of the polycrystalline silicon substrate as a criterion value.

13. The device of claim 1, wherein the camera divides the captured image into a grid of cells to calculate an intensity of light in each of the cells, and it is determined that a crystallinity in a cell is abnormal when a calculated intensity of light of the cell is out of an error margin of a predetermined intensity of light.

14. The device of claim 1, wherein the light source comprises a plurality of light sources disposed below the polycrystalline silicon substrate at a regular spacing, and the polarizing plate has such an area that it covers the polycrystalline silicon substrate.

* * * * *